(12) United States Patent
Karahalios et al.

(10) Patent No.: US 8,069,755 B2
(45) Date of Patent: *Dec. 6, 2011

(54) DEVICES AND METHODS FOR CUTTING A VERTEBRAL IMPLANT

(75) Inventors: Dean G. Karahalios, Lake Forest, IL (US); Danny Horton Braddock, Jr., Germantown, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/907,688

(22) Filed: Oct. 19, 2010

(65) Prior Publication Data

US 2011/0034929 A1   Feb. 10, 2011

Related U.S. Application Data

(63) Continuation of application No. 11/475,362, filed on Jun. 27, 2006, now Pat. No. 7,819,043.

(51) Int. Cl.
*B23B 3/22* (2006.01)
*B23Q 1/40* (2006.01)

(52) U.S. Cl. .......................... 82/1.11; 82/113
(58) Field of Classification Search ............ 82/1.11, 82/113, 117, 118
See application file for complete search history.

(56) References Cited

U.S. PATENT DOCUMENTS

| | | | | |
|---|---|---|---|---|
| 4,625,464 A * | 12/1986 | Kubo | ............ | 451/441 |
| 5,549,024 A * | 8/1996 | Ricci | ............ | 82/113 |
| 6,557,226 B1 * | 5/2003 | Landry et al. | ............ | 29/27 C |
| 7,819,043 B2 * | 10/2010 | Karahalios et al. | ............ | 82/1.11 |
| 2003/0045882 A1 * | 3/2003 | Gwyther | ............ | 606/79 |
| 2005/0125986 A1 * | 6/2005 | Pham et al. | ............ | 29/557 |

* cited by examiner

Primary Examiner — Will Fridie, Jr.

(57) ABSTRACT

The present application is directed to devices and methods for cutting a spinal implant. In one embodiment, the device includes a handle and a head. The handle is sized to receive a predetermined length of the implant. A head is rotatably attached to the handle and includes a blade. After the implant is inserted into the handle, the head is rotated causing the blade to move around the implant and cut an excessive length from the predetermined length.

20 Claims, 5 Drawing Sheets

DEVICES AND METHODS FOR CUTTING A VERTEBRAL IMPLANT

RELATED APPLICATION

This application is a continuation of co-pending application Ser. No. 11/475,362, filed on Jun. 27, 2006, and herein incorporated by reference in its entirety.

BACKGROUND

The present application is directed to devices and methods for cutting a vertebral implant, and more particularly, to tools and methods for cutting an elongated implant to a desired length.

The spine is divided into four regions comprising the cervical, thoracic, lumbar, and sacrococcygeal regions. The cervical region includes the top seven vertebral members identified as C1-C7. The thoracic region includes the next twelve vertebral members identified as T1-T12. The lumbar region includes five vertebral members L1-L5. The sacrococcygeal region includes nine fused vertebral members that form the sacrum and the coccyx. The vertebral members of the spine are aligned in a curved configuration that includes a cervical curve, thoracic curve, and lumbosacral curve. Intervertebral discs are positioned between the vertebral members and permit flexion, extension, lateral bending, and rotation.

Various conditions may lead to damage of the intervertebral discs and/or the vertebral members. The damage may result from a variety of causes including a specific event such as trauma, a degenerative condition, a tumor, or infection. Damage to the intervertebral discs and vertebral members can lead to pain, neurological deficit, and/or loss of motion.

Various procedures include replacing the entirety or a section of a vertebral member, the entirety or a section of an intervertebral disc, or both. One or more replacement implants may be inserted to replace the damaged vertebral members and/or discs. The implants reduce or eliminate the pain and neurological deficit, and increase the range of motion. The size of the implant is carefully measured to match the existing anatomy.

SUMMARY

The present application is directed to various devices and methods for cutting an elongated vertebral implant. The device may include a handle with an elongated receptacle that extends along a longitudinal axis and is sized to receive the implant. The receptacle may include an open front end, a back member, and an intermediate side that extends between the open front end and the back member. The longitudinal axis may extend through the open front end and the back member. A blade may be rotatably attached to the handle at the open front end and may be adjustable in a radial direction relative to the longitudinal axis. The receptacle may be sized to receive the implant through the open front end with a length of the implant within the receptacle and an excess length extending outward beyond the blade. Rotation of the blade relative to the handle may cause the blade to move around the implant and cut the excess length of the implant.

The device may also include a frame with an interior space formed by first and second annular members and a number of longitudinal members that are attached to and extend between the annular members. The longitudinal members may be spaced around perimeters of the first and second annular members. A longitudinal axis may extend along the longitudinal members and through openings associated with the first and second annular members. A blade may be rotatably attached to the first annular member and may be adjustable in a radial direction relative to the longitudinal axis. Rotation of the blade relative to the frame may move the blade to cut the implant into a first portion disposed in the interior space and a second portion extending outwardly from the interior space beyond the blade.

The device may also include a handle with an elongated receptacle with an open end and a back spaced from the open end. The receptacle may be sized to receive the implant and may include a longitudinal axis that extends through the open end and the back. A depth limiter may be secured to the back and movable within the receptacle along the longitudinal axis. A blade may be operatively connected to the handle and may be adjustable in a radial direction relative to the longitudinal axis. The implant may be insertable through the opening and the open end and into the receptacle with the implant in contact with the depth limiter to position a predetermined length of the implant within the receptacle with an excess length extending outward beyond the blade. Rotation of the blade relative to the handle may cause the blade to move around the implant and cut the excess length of the implant from the predetermined length.

DETAILED DESCRIPTION

The present application is directed to devices and methods for cutting a spinal implant. The devices generally include a receptacle for holding the implant and a blade. The implant is positioned within the receptacle and aligned at a predetermined position relative to the blade. The blade can rotate relative to the handle to move around and cut into the implant at the predetermined position.

Figure 1:
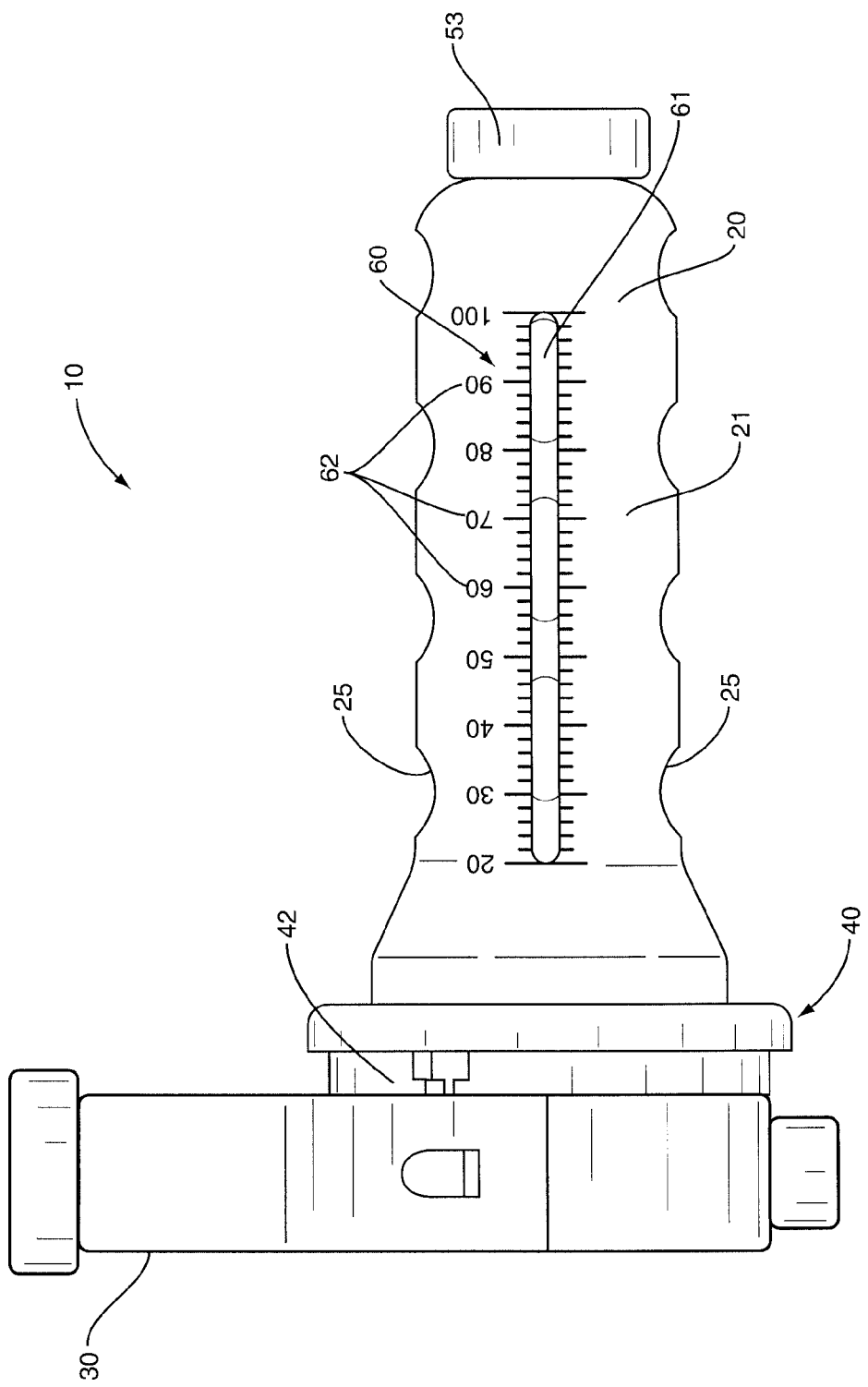
FIG. 1 is a side view of a device according to one embodiment.
Figure 2:
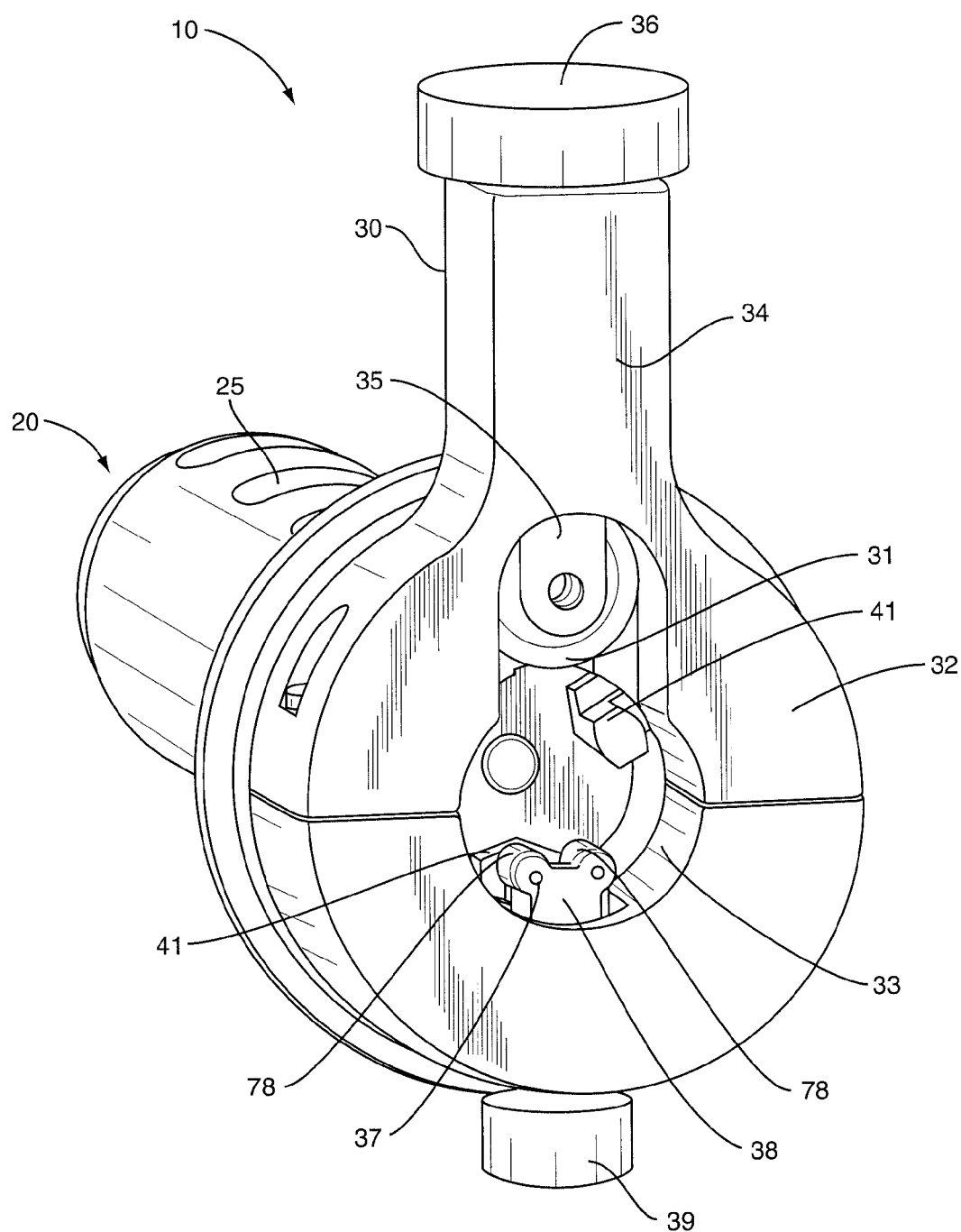
FIG. 2 is a perspective view of a device according to one embodiment.

FIG. 1 illustrates one embodiment of a device 10 that generally includes a handle 20 and a head 30. The handle 20 is sized to receive a length of the implant 100 and the head 30 includes a blade 31 (FIG. 2). The head 30 is rotatably mounted to the handle 20 with rotation causing the blade 31 to move around and cut the implant 100.

Figure 3:
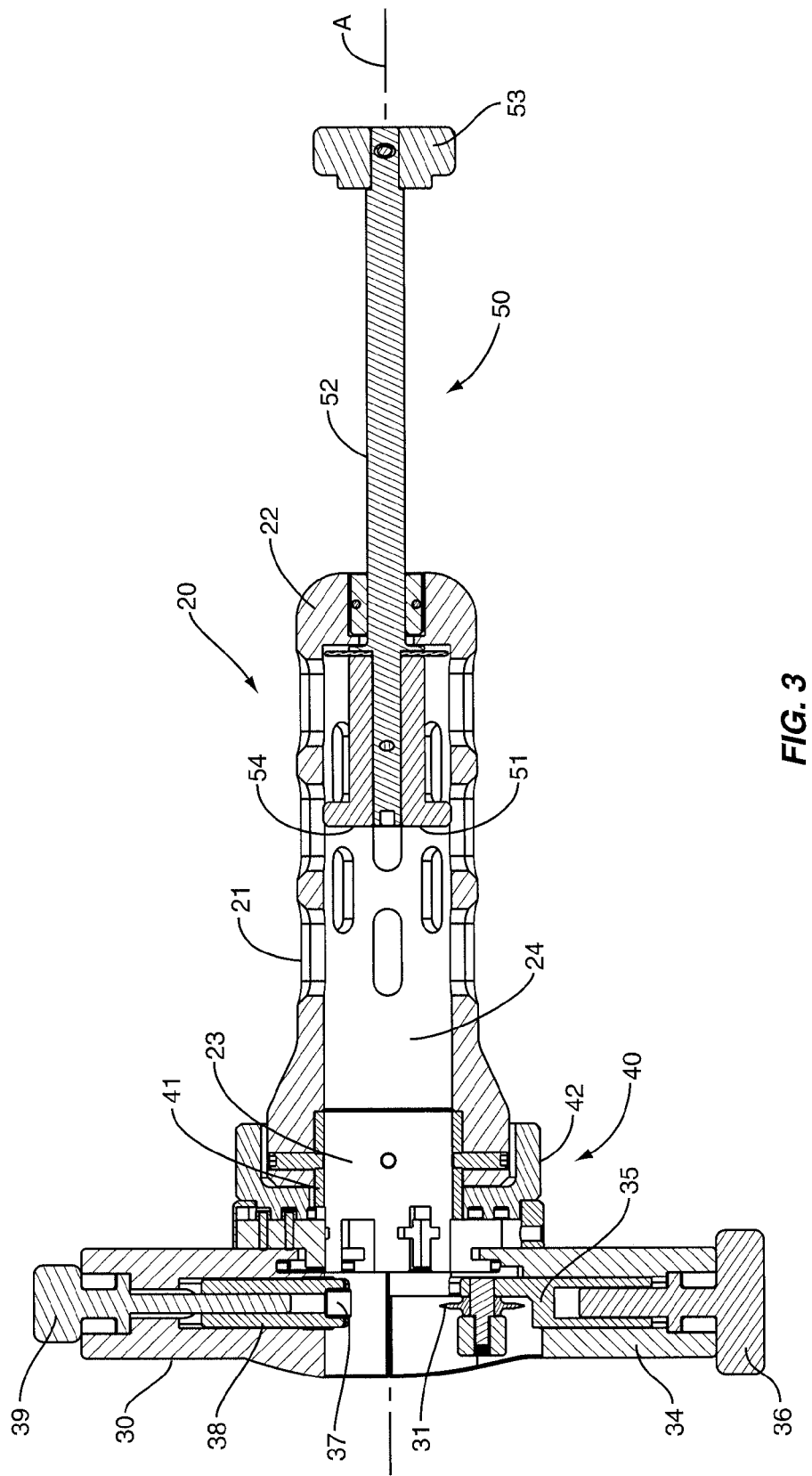
FIG. 3 is a cross-section view of a device according to one embodiment.
Figure 5:
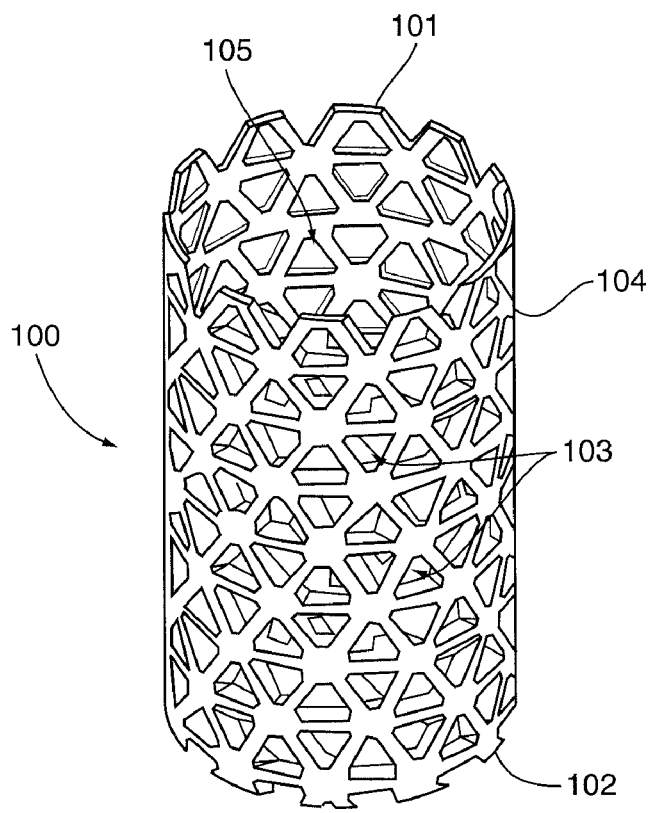
FIG. 5 is a perspective view of an implant according to one embodiment.

The handle 20 receives the implant 100 during the cutting process. Handle 20 includes a receptacle 24 formed by sidewalls 21 and a second end 22. The handle 20 may have a cylindrical shape that is larger than the cylindrical implant 100 (see FIG. 5). The sidewalls 21 and second end 22 may be solid to form an enclosed interior space, or may include one or more openings. A first end 23 is open and leads into the receptacle 24. The receptacle 24 may include a substantially constant diameter along the length between the first and second ends, or may include a variable diameter. The receptacle 24 includes an elongated shape that may be centered about a longitudinal axis A as illustrated in FIG. 3.

In one embodiment as illustrated in FIG. 1, the handle 20 is substantially cylindrical to provide an effective structure for a user to grasp during the cutting procedure. To further facilitate holding, one or more grips 25 may be positioned on the exterior of the handle 20. The exterior may further include a roughened or knurled surface over portions or the entirety to prevent slipping while holding the handle 20.

A holder 40 may be positioned to hold the implant 100 within the receptacle 24 and prevent the implant 100 from rotating during the cutting process. In one embodiment, the holder 40 includes one or more jaws 41 that move into the receptacle 24 to contact and prevent the implant 100 from rotating within the receptacle 24. The jaws 41 are movable in a radial direction relative to the longitudinal axis A of the receptacle 24. In one embodiment, the jaws 41 move substantially perpendicular to the axis A. Jaws 41 move between a retracted orientation that is away from the center of the receptacle 24, and an extended orientation that is towards the axis A. The adjustability of the jaws 41 provide for receiving implants 100 of different diameters within the receptacle 24. By way of example, an implant 100 with a smaller diameter may require the jaws move to a more extended position to hold the implant than required for a larger diameter implant.

Figure 6:
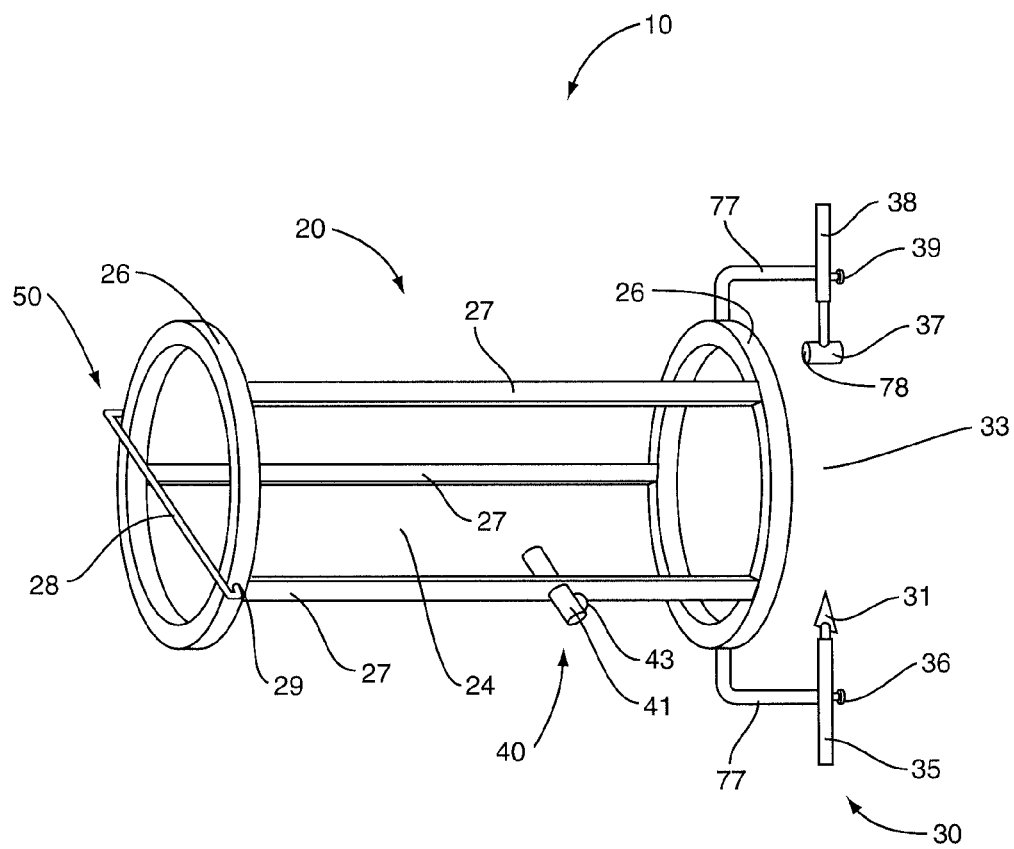
FIG. 6 is a perspective view of a device according to one embodiment.

Various numbers of jaws 41 may be positioned in the receptacle 24. In one embodiment, three separate jaws are angularly spaced about the receptacle 24 to contact and hold the implant 100. The jaws 41 may be evenly or unevenly spaced around the periphery. In an embodiment with three jaws 41, the jaws 41 are spaced about 120° apart. In another embodiment as illustrated in FIG. 6, a single jaw 41 is mounted on the handle 20 to move into and out of the receptacle 24.

Figure 4:
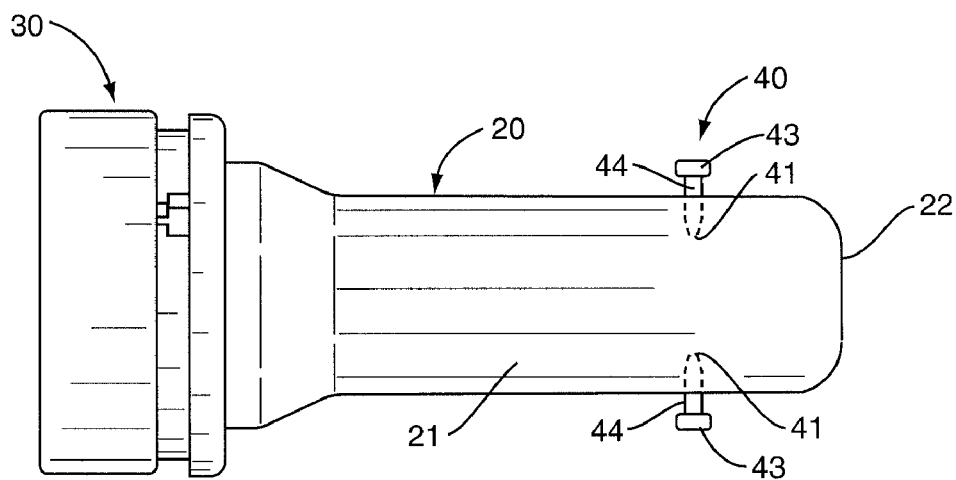
FIG. 4 is a side view of a device according to one embodiment.

The jaws 41 may be radially adjusted in a number of different manners. In one embodiment as illustrated in FIGS. 1 and 3, the jaws 41 are positioned within a chuck 42. The chuck 42 is rotated to move the jaws 41 in a radial direction relative to the longitudinal axis A. In another embodiment as illustrated in FIG. 4, the jaws 41 are attached to an end of a shaft 44 that is threadingly engaged within the sidewall 21 and extends into the receptacle 24. Knobs 43 may be positioned opposite from the jaws 41 to rotate the shafts 44 and radially move the position of the jaws 41. FIG. 6 illustrates another embodiment with a single jaw 41 mounted on a support member 27 of the handle 20.

The holder 40 may be positioned at a variety of locations along the device 10. In the embodiments of FIGS. 1 and 3, holder 40 is positioned towards the open end 23 of the receptacle 24. FIGS. 4 and 6 illustrate embodiments with the holder 40 positioned away from the open end 23. Also, multiple holders 40 may be included within a single device 10. By way of example, a first holder 40 may be positioned at the open end 23, and a second holder 40 may be positioned towards the second end 22. In the various embodiments, the holders 40 may include one or more jaws 41, and in devices with multiple holders 40, the holders 40 may be of the same or a different construction.

A length adjuster 50 may be operatively connected to the handle 20 to adjust a length of the receptacle 24. FIG. 3 illustrates one embodiment of a length adjuster 50 that includes a stopper 51 with a contact surface 54 positioned within the receptacle 24. The stopper 51 is attached to an arm 52 that extends through the second end 22 of the handle 20 and terminates at a knob 53. The stopper 51 is axially movable within the receptacle 24 to adjust a length that extends between the contact surface 54 and the blade 31. The length adjuster 50 may be slidable within the handle 20 by the user applying a pushing and pulling force through the knob 53. In another embodiment, the arm 52 includes threads (not illustrated) that engage with a threaded opening in the second end 22. Movement of the length adjuster 50 is accomplished by rotating the knob 53 in first and second directions.

FIG. 6 illustrates another length adjuster 50 that includes a stop 28 mounted to a rib 26 of the handle 20. The stop 28 may be fixedly positioned, or may be movable. In one embodiment, the ends 29 of the stop 28 include ramped surfaces that correspond to ramps on the rib 26. The stop 28 may be moved inward and outward along the longitudinal axis A with the ramps engaging and setting the length of the receptacle 24.

A measurement scale 60 may be associated with the handle 20 for the user to select the desired length formed between the contact surface 54 of the length adjuster 50 and the blade 31. FIG. 1 illustrates an embodiment that includes a window 61 within the sidewall 21 of the handle 20. This window 61 is an elongated opening that allows the user to visually look into the interior space of the receptacle 24. Window 61 may further include a light transmissive member, such as a clear plastic or glass piece. Length increments 62 may be positioned along the window 61 to indicate the distance from the blade 31. In another embodiment as illustrated in FIG. 6, length increments are indicated near the ends 29 of stop 28. The increments align with the rib 26 to indicate the length of the receptacle 24.

The head 30 is rotatably mounted to the handle 20 and positions the blade 31. As best illustrated in FIG. 2, the head 30 may include a body 32 with an opening 33. The head 30 is mounted to the handle 20 with the opening 33 aligning with the open end 23 of the receptacle 24. A center of the opening 33 may be aligned with the longitudinal axis A of the receptacle 24. The body 32 may extend completely around the opening 33, or may extend around a limited section of the opening 33. An extension 34 may extend outward from the body 32 and provide a grasping point for the user to grasp to rotate the head 30.

The blade 31 is attached to the head 30 to contact and cut the implant 100 during rotation of the head 30. The blade 31 may include a variety of shapes and configurations. In one embodiment, blade 31 is substantially circular with an opening in the interior to receive a fastener for attachment to the head 30. In some embodiments, a single blade 31 is attached to the head 30. Other embodiments may include two or more blades 31 that are each attached to the head 30. The blades 31 may have the same or different construction.

As illustrated in FIGS. 2 and 3, one or more arms 35 may be positioned within the head 30 to hold and position the blade 31. In one embodiment, a pair of arms 35 are spaced apart with an intermediate gap sized to receive the blade 31. A fastener (not illustrated) may extend through the blade 31 and attach to the arms 35. A knob 36 may be threadingly engaged with the arms 35 with rotation of the knob 36 causing the blade 31 to move within the opening 33 and move radially relative to the longitudinal axis A.

One or more support members 37 may be attached to the head 30 and work in combination with the blade 31 to cut the implant 100. In the embodiment of FIGS. 2 and 3, a single support member 37 is positioned opposite from the blade 31 (i.e., about 180° apart). The support member 37 assists in maintaining the implant 100 positioned against the blade 31 during rotation of the head 30. The support member 37 may be mounted on arms 38 for radial movement relative to the longitudinal axis A. A knob 39 is threadingly engaged with the arms 38 with rotation of the knob 39 causing the support member 37 to move in a radial direction towards and away from the longitudinal axis A.

Support member 37 may include a variety of configurations. FIG. 2 illustrates an embodiment with a pair of rollers 78 positioned at the end of the arms 38. The rollers 78 are rotatably connected to the arms 38 and extend outward to contact the implant 100. The rollers 78 contact and rotate about the stationary implant 100 during rotation of the head 30. FIG. 6 illustrates an embodiment with a single roller 78.

The device 10 is used for cutting an implant 100 to a desired size. One application of the device 10 is for cutting a corpectomy cage, such as that illustrated in FIG. 5. The implant 100 is generally cylindrical with a hollow interior 105 and extends between first and second ends 101, 102. The implant 100 may include openings 103 that extend through the sidewalls 104 and into the hollow interior 105. The implant 100 may be constructed of a variety of materials such as titanium and stainless steel. One specific type of material is PYRAMESH available from Medtronic Sofamor Danek of Memphis, Tenn. The implant 100 may further be used with end caps (not illustrated) that are attached at the first and second ends 101, 102 and contact the vertebral members. One embodiment is disclosed in U.S. Pat. No. 6,776,798. The device 10 may further be used for cutting various other implants 100, such as a cylindrical tube without openings.

In use, the implant 100 is inserted through the open end 23 of the handle 20 and into the receptacle 24. The length adjuster 50 may be adjusted according to the contact surface 54 positioned at a desired distance away from the blade 31. Once the implant 100 is positioned in the receptacle 24 at the predetermined position, the holder 40 may be tightened to prevent the implant 100 from rotating. This may include rotating the chuck 42 and moving the one or more jaws 41 radially inward towards the longitudinal axis A and in contact with the implant 100. This may also include rotating the knobs 43 and moving the jaws 41 into contact with the implant 100.

Once the implant 100 is held within the receptacle 24, the blade 31 may be moved into contact with the implant 100. This may require the knob 36 to be rotated to radially move the blade 31 into contact. In embodiments with support members 37, the members 37 are also radially moved into contact with the implant 100.

To cut the implant 100, the user may grasp the device 10 with a first hand at the handle 20 with their fingers aligning with the grips 25 on the exterior surface. The user may then use their second hand to rotate the head 30 relative to the handle 20. This rotation contacts the blade against the outer circumference of the implant 100 and cuts into the implant 100. In some embodiments, the head 30 is rotated a number of times with the blade 31 cutting a first distance into the implant 100. The blade 30 is then radially moved a further amount. This further blade movement occurs by further rotating the knob 36 that is associated with the blade 31. The head 30 is again rotated and the an additional distance is cut into the implant 100. The number of additional radial movements of the blade 31 may be dependent upon the thickness of the implant 100 and/or the implant material. In one embodiment, the implant 100 and the blade 31 are centered about the longitudinal axis A. Therefore, the blade 31 cuts evenly into the implant 100 during the complete rotation.

Continued rotation of the head 30 causes the blade 31 to eventually cut through the sidewall 104 of the implant 100 causing the section of the implant that extends beyond the blade 31 to be severed from the section that is held by the device 10. After completion of the cut, the blade 31 and jaw 41 are each moved radially away from the longitudinal axis A. If the device includes a support roller 37, it also is moved away. The implant 100 may then be removed from the receptacle 24.

The implants 100 that are sized using these devices and methods may be used within the various regions of the spine, including the cervical, thoracic, lumbar and/or sacral portions of the spine.

Spatially relative terms such as "under", "below", "lower", "over", "upper", and the like, are used for ease of description to explain the positioning of one element relative to a second element. These terms are intended to encompass different orientations of the device in addition to different orientations than those depicted in the figures. Further, terms such as "first", "second", and the like, are also used to describe various elements, regions, sections, etc and are also not intended to be limiting. Like terms refer to like elements throughout the description.

As used herein, the terms "having", "containing", "including", "comprising" and the like are open ended terms that indicate the presence of stated elements or features, but do not preclude additional elements or features. The articles "a", "an" and "the" are intended to include the plural as well as the singular, unless the context clearly indicates otherwise.

The present invention may be carried out in other specific ways than those herein set forth without departing from the scope and essential characteristics of the invention. The present embodiments are, therefore, to be considered in all respects as illustrative and not restrictive, and all changes coming within the meaning and equivalency range of the appended claims are intended to be embraced therein.

What is claimed is:

1. A device to cut an elongated spinal implant comprising:
a handle including an elongated receptacle that extends along a longitudinal axis and is sized to receive the implant, the receptacle including an open front end, a back member, and an intermediate side that extends between the open front end and the back member, the longitudinal axis extends through the open front end and the back member;
a blade rotatably attached to the handle at the open front end and being adjustable in a radial direction relative to the longitudinal axis;
the receptacle sized to receive the implant through the open front end with a length of the implant within the receptacle and an excess length extending outward beyond the blade; and
rotation of the blade relative to the handle causes the blade to move around the implant and cut the excess length of the implant.

2. The device of claim 1, further comprising a depth limiter attached to the handle and extending through the back member, the depth limiter being movable along the longitudinal axis to control a depth of the receptacle.

3. The device of claim 2, wherein the depth limiter includes an arm that extends through the back member and a contact member attached to an end of the arm that is positioned in the receptacle, the contact member includes a contact surface that faces towards the open end.

4. The device of claim 1, further comprising at least one jaw positioned within the receptacle to contact the implant and prevent the implant from rotating during rotation of the blade.

5. The device of claim 1, further comprising a plurality of indentations positioned along an exterior of the handle to form a grip to hold the device.

6. The device of claim 1, further comprising a knurled section extending along at least a section of an exterior of the handle.

7. The device of claim 1, wherein the back member extends completely across the receptacle.

8. The device of claim 7, wherein the back member completely encloses the receptacle opposite from the open front end.

9. The device of claim 1, further comprising a window formed along the intermediate side of the handle between the open front end and the back member, the window providing visual access into the receptacle.

10. The device of claim 9, wherein the window includes a plurality of length increments forming a measurement scale for measuring a length of the implant inserted into the receptacle.

11. A device to cut an elongated spinal implant comprising:
   a frame comprising an interior space formed by first and second annular members and a plurality of longitudinal members attached to and extending between the annular members, the longitudinal members spaced around perimeters of the first and second annular members, wherein a longitudinal axis extends along the longitudinal members and through openings associated with the first and second annular members; and
   a blade rotatably attached to the first annular member, the blade being adjustable in a radial direction relative to the longitudinal axis;
   wherein rotation of the blade relative to the frame moves the blade to cut the implant into a first portion disposed in the interior space and a second portion extending outwardly from the interior space beyond the blade.

12. The device of claim 11, wherein the longitudinal members are evenly spaced around the perimeters of the first and second members.

13. The device of claim 11, further comprising a depth limiter mounted to the second annular member and including a contact member positioned in the interior space between the first and second annular members.

14. The device of claim 13, wherein the depth limiter is movable through the second annular member and along the longitudinal axis.

15. The device of claim 11, further comprising at least one holding element positioned within the interior space and adjustable in a radial direction relative to the longitudinal axis to contact the implant and prevent movement during rotation of the blade.

16. The device of claim 11 further comprising a scale disposed along at least one of the longitudinal members.

17. A device to cut an elongated spinal implant comprising:
   a handle comprising an elongated receptacle with an open end and a back spaced from the open end, the receptacle being sized to receive the implant and includes a longitudinal axis that extends through the open end and the back;
   a depth limiter secured to the back and movable within the receptacle along the longitudinal axis;
   a blade operatively connected to the handle and being adjustable in a radial direction relative to the longitudinal axis;
   the implant insertable through the opening and the open end and into the receptacle with the implant in contact with the depth limiter to position a predetermined length of the implant within the receptacle with an excess length extending outward beyond the blade;
   wherein rotation of the blade relative to the handle causes the blade to move around the implant and cut the excess length of the implant from the predetermined length.

18. The device of claim 17, wherein the depth limiter is operatively connected to the handle and includes a member having a contact surface, the member being movably positioned within the receptacle along the longitudinal axis to adjust a distance between the contact surface and the open end.

19. The device of claim 17, further comprising a scale disposed along the handle to measure the predetermined length of the implant within the receptacle.

20. The device of claim 17, wherein the back extends across the receptacle.

* * * * *